United States Patent [19]

Shanbrom

[11] Patent Number: 4,933,169

[45] Date of Patent: Jun. 12, 1990

[54] ANTIVIRAL INHALATION THERAPY

[76] Inventor: Edward Shanbrom, 2252 Liane La., Santa Ana, Calif. 92705

[21] Appl. No.: 321,521

[22] Filed: Mar. 9, 1989

Related U.S. Application Data

[63] Continuation-in-part of Ser. No. 276,113, Nov. 23, 1988, abandoned, and a continuation-in-part of Ser. No. 290,161, Dec. 28, 1988, Pat. No. 4,891,221.

[51] Int. Cl.$^5$ ......................... A61K 9/14; A61K 31/19
[52] U.S. Cl. .......................................... 424/46; 424/43; 514/34; 514/557; 514/572
[58] Field of Search ............................... 514/557, 572; 424/43–47

[56] References Cited

U.S. PATENT DOCUMENTS 3,944,660  3/1976  Gottfried et al. ...................... 424/43
4,540,567  9/1985  Oneto et al. .......................... 424/45

OTHER PUBLICATIONS

Yoshida–Chem. Abst. vol. 105 (1986) p. 196,993e.

*Primary Examiner*—Sam Rosen
*Attorney, Agent, or Firm*—Grant L. Hubbard

[57] ABSTRACT

Methods and compositions for treating infectious diseases comprising introducing such compositions, which consist essentially of one or more glycyrrhizie triterpenoid compounds, such as, for example, carbenoxolone, glycyrrhizin or cicloxolone, are disclosed. Therapy by inhalation is contemplated.

6 Claims, No Drawings

ANTIVIRAL INHALATION THERAPY

CROSS-REFERENCE TO RELATED APPLICATION

This is a continuation-in-part of U.S. patent applications Ser. Nos. 276,113, filed Nov. 23, 1988, now abandoned, and 290,161 filed Dec. 28, 1988, now U.S. Pat. No. 4,891,221 to which priority is claimed.

FIELD OF THE INVENTION

This invention relates methods for treating humans and other animals with aerosols or nebulized compositions to prevent or inhibit the infection of the subject by viral diseases and/or to treat the subject to cure or interfere with the progress of virus caused infectious diseases.

BACKGROUND OF THE INVENTION

Virus caused respiratory illnesses account for much of the suffering and inconvenience endured by mankind and animals generally, and, in some instances, account for high rates of mortality.

Influenza is one of the common diseases of man, infecting large segments of the population each year, typically during the fall and winter and early spring of the year, with great economic consequences and, occasionally, with great public health consequences. For example, more people died in the influenza epidemic of 1918 than died in World War I. Certain members of the family orthomyxoviridae infect humans, animals and birds, while certain other members infect only humans. Orthomyxoviridae, or flu virus, is an enveloped RNA virus consisting basically of an internal nucelocapsid and an envelope made up of a matrix protein, a lipid bilayer, and externalglycoproteins.

Notwithstanding that influenza has been extensively studied, very little progress has been made toward the prevention or cure of the disease. One reason for the slow progress toward preventing or treating influenza is the antigenic shift which presents frequent and often abrupt appearances of new serotypes with the consequence that an inactivated virus vaccine against one serotype may have little or no immunizing effect against other serotypes. It has, thus far, impossible to develop a single vaccine against all influenza based on antigenic determinants.

Influenza A and B viruses exhibit frequent minor antigenic drift and type A viruses undergo a major antigenic shift every one to four decades, thus assuring that at least a portion of the population is always susceptible. Children and young adults have the highest incidence of influenza infection each winter, but the highest incidences of severe or complicated influenza illness leading to hospitalization or death are in infants, elderly persons (especially those in nursing homes), and persons of all ages with underlying heart or lung disease. Influenza viruses infect respiratory epithelial cells and can themselves cause diffuse pulmonary infiltrates and severe hypoxia, but concomitant or secondary bacterial pneumonia is a much more frequent complication of influenza. (Influenza pneumonia, Ruben FL; Cate TR, *Semin Respir Infect* Jun 1987, 2 (2) p122–9.)

Members of the family paramyxoviridae are responsive for a number of serious diseases in humans and animals. Bronchiolitis is one of the most serious pulmonary infections commonly caused by respiratory syncytial virus (RSV), a member of the paramyxoviridae. RSV disease occurs in yearly epidemics and is most severe in children 1 year of age or younger. Approximately 1 in 50 to 1 in 100 infants are hospitalized after their first infection, and mortality fluctuates between 0.5 and 5.0 per cent. Patients with underlying conditions such as congenital heart disease and bronchopulmonary dysplasia are at higher risk for morbidity and mortality. Respiratory syncytial virus disease has also been documented in immunocompromised adults, aged 21 to 50, wherein the immune system had been comprised by bone marrow transplants, renal transplants, pancreas transplants and by T-cell lymphoma, based on specimens from bronchoalveolar lavage, sputum, throat, sinus aspirate, and lung biopsy. (Respiratory syncytial virus infection in immunocompromised adults, Englund JA; Sullivan CJ; Jordan MC; Dehner LP; Vercellotti GM; Balfour HH Jr, *Ann Intern Med* Aug 1 1988, 109 (3) p203–8.)

Pneumonias in adults due to mycoplasma, chlamydiae, and viruses are a common clinical problem. These microorganisms contribute to the etiologies in 6–35% of all cases of pneumonia and are the sole pathogens in 1–17% of hospitalized cases. Important trends and developments in the field include the emergence of a Chlamydia psittaci strain (TWAR) that is passaged from human to human, causes a mycoplasma-like illness, and that is relatively resistant to erythromycin, and the recognition of respiratory syncytial virus as a pathogen in nursing home outbreaks and in immunosuppressed adults, the continuing high lethality of fully developed influenza pneumonia, the efficacy of acyclovir and adenine arabinoside in limiting the complications of varicella-zoster virus infections, and the increasing frequency of pneumonia caused by cytomegalovirus and the severity of this disorder in highly immunosuppressed patients. Developments in the rapid diagnosis and therapy of respiratory syncytial virus infections with an aerosolized antiviral drug in children may pave the way for comparable advances in difficult pneumonias in adult patients. (Pneumonias in adults due to mycoplasma, chlamydiae, and viruses, Luby JP, *Am J Med Sci* Jul 1987, 294 (1) p45–64.)

Cytomegalovirus (CMV) pneumonia causes significant morbidity and mortality in bone marrow transplant recipients and in patients with AIDS. 9-(1,3-Dihydroxy-2-propoxymethyl) guanine (ganciclovir) and phosphonoformic acid (PFA) demonstrate activity against CMV in human infections, although recurrent CMV and systemic drug toxicity frequently develop. The efficacy of aerosol administration of antiviral agents against murine CMV (MCMV) infection has been examined using aerosolized ganciclovir, PFA, or ribavirin. The results suggest that aerosol administration of antiviral agents can potently and selectively inhibit replication of MCMV in the lung. (Aerosol administration of antiviral agents to treat lung infection due to murine cytomegalovirus. Debs RJ; Montgomery AB; Brunette EN; DeBruin M; Shanley JD, *J Infect Dis* (UNITED STATES) Feb 1988, 157 (2) p327–31.)

Broad spectrum anti-viral agents have only recently appeared and have not yet been established as generally efficacious, but have shown great promise in a few areas. (Antiviral agents, Hermans PE; Cockerill FR 3d, *Mayo Clin Proc* Dec 1987, 62 (12) p1108–15.) Progress is, however, being made in the development of drugs for the prevention and treatment of viral respiratory infections. Two drugs currently available to clinicians are amantadine (Symmetral) and ribavirin (Virazole). Oral amantadine is effective for both treatment and prevention of uncomplicated influenza A infections. Although vaccination continues as the mainstay of influenza prevention, amantadine is useful for unvaccinated patients if complications are likely. Ribavirin appears to be safe for treatment of respiratory syncytial virus infections in nonintubated infants. It must, however, be delivered by aerosol in a hospital setting. Another drug, rimantadine is similar to amantadine in its action and indications for use and has a lower incidence of side effects. (Antiviral drugs for common respiratory diseases. What's here, what's to come, Johnson DC, *Postgrad Med* Feb 1 1988, 83 (2) p136–9, 142–3, 146–8; *Postgrad Med* 1988 Apr;83(5):52.)

Aerosol or nebulizer inhalation therapy has been established as effective in treating, and possibly in preventing, certain virus induced diseases. Aerosol treatment using ribavirin was shown to alleviate the symptoms of influenza and to reduce the shedding of influenza virus from the respiratory tract, (Ribavirin aerosol treatment of influenza, Knight V; Gilbert BE, *Infect Dis Clin North Am* (UNITED STATES) Jun 1987, 1 (2) p441–57.) and with amantadine. (Favorable outcome after treatment with amantadine and ribavirin in a pregnancy complicated by influenza pneumonia. A case report. Kirshon B; Faro S; Zurawin RK; Samo TC; Carpenter RJ, *J Reprod Med* Apr 1988, 33 (4) p399–401.) Ribavirin aerosol is now used with some success in the treatment of RSV infections. (Ribavirin aerosol treatment of serious respiratory syncytial virus infection in infants, Rodriguez WJ; Parrott RH, *Infect Dis Clin North Am* (UNITED STATES) Jun 1987, 1 (2) p425–39.)

While some progress is being made in the field of inhalation therapy of virus caused infectious diseases, it is apparent from the foregoing discussion there remains a great need for improved methods of killing or inactivating pathogenic viruses in the respiratory tract of animals generally, and of man in particular.

SUMMARY OF THE INVENTION

The present invention is embodied in apparatus for treating animals generally and humans in particular with one or more glycyrrhizic triterpenoid compounds in the form of an aerosol by inhalation therapy to prevent, or inhibit the contraction of, and/or to treat certain diseases caused by virus infections.

One or more glycyrrhizic triterpenoid compounds in a concentration of from 0.05 to 10.0 wt/%, preferable from 0.5 to 3 wt/%, in combination with suitable carrier or solvent, and, if desired, with a penetration enhancer, such as azone or dimethyl sulfoxide, for example, is introduced from a neubulizer as an aerosol into the respiratory tract of the subject either periodically or on a continuous basis for an extended period of time.

Thus, the present invention comprises methods for inactivating viruses the respiratory tract, i.e. the mouth or nose, throat and lungs, by the use of extracts of the well-known flavoring agent licorice, referred to here as glycyrrhizic triterpenoids or GTPD compounds.

DESCRIPTION OF THE PREFERRED EMBODIMENT

Glycyrrhizic acid, 20-B-carboxy-11-oxo-30-norolean-12-en-3B-yl-2-O-B-D-glucopyranuronsyl-a-D-glucopyranosiduronic acid, commonly known as glycyrrhizin, glycyrrhizinic acid or glycyrrhetinic acid glycoside (also referred to as biosone, enoxolone, and glycyrrhetin), an extract from Glycyrrhiza, better known as licorice, an extract of the dried rhizome and roots of Glycyrrhiza glabra, is a triterpene and is exemplary of the triterpenes to which this invention relates. Analogous triterpenes to which this invention relates include carbenoxolone and cicloxolone. This invention thus relates to glycyrrhizic acid and analogues thereof, in the form of acids, salts, esters and other derivatives. Many such derivatives are known, such as, for example: Glycyrrhisoflavone; Benzyl glycyrrhetinate; Glycyrrhizinic acid ammonium salt; Glycyrrhizinic acid hydrolase; Glycyrrhizinic acid; Zinc glycyrrhizinate; Glycyrrhetic acid 3-0-(hydrogen sulfate); Glycyrrhetinyl stearate; Monopotassium glycyrrhetin; 3-Oxo-18-a-glycyrrhetinic acid; 11-Deoxoglycyrrhetinic acid hydrogen maleate sodium salt; 11-Deoxoglycyrrhetinic acid hydrogen maleate; 18-a-Glycyrrhizic acid diammonium salt; Monoarginine glycyrrhizinate; Potassium glycyrrhizinate; 18-a-Glycyrrhizinic acid; 18-a-Glycyrrhizic acid monosodium salt; 18-a-Glycyrrhizic acid dipotassium salt; 18-a-Glycyrrhizic acid disodium salt; 18-a-Glycyrrhizic acid monopotassium salt; Glycyrrhizinic acid mono-triethanolamine) salt; Glycyrrhizinic acid disodium salt; Trisodium glycyrrhizinate; Dipotassium glycyrrhizate; Triammonium glycyrrhizinate; Dioxoglycyrrhetinic acid; Sodium glycyrrhizate; Ammonium glycyrrhizinate; Tripotassium glycyrrhizate; Glycyrrhetinic acid nicotinate morpholine salt; Benzyl 3-0-benzyl-18-Bglycyrrhetate; 3-0-Acetylglycyrrhetaldehyde; Glycyrrhizic acid monopotassium salt; Magnesium di-3-acetyl-18-B-glycyrrhetinate; Magnesium monomethoxymono-3-acetyl-18-B-glycyrrhetinate; Dehydrocorydaline glycyrrhizate; Ruscogenin acetylglycyrrhetinate; Glycyrrhetic acid 3-0-glucuronide; Cinoxolone; crotyl glycyrrhetate; Glycyrrhizin trimethyl ester; 3-0-Acetylglycyrrhetoyl chloride; Aluminum acetylglycyrrhetate; Dipotassium glycyrrhetinate; Methyl 11-deoxo-18-aglycyrrhetate; Calcium potassium glycyrrhizinate; Glycyrrhetic acid monophosphate; B-glycyrrhetinicacid 3-acetate; 24-Hydroxyglycyrrhetic acid; 3-0-Acetyl-18-B-glycyrrhetamide; Deoxyglycyrrhetic acid; N-(18-B-Glycyrrhetyl)glycine; 3-0-Propionyl-18-B-glycyrrhetic acid; o-(18-B-Glycyrrhetamideo)benzoic acid; Glycyrrhetol; Stearyl glycyrrhetinate; Glycyrrhizic acid monosodium salt; Methyl 3-0-acetylglycyrrhetinate; Carbenoxolone sodium; Ammonium glycyrrhetinate; 3-Dehydro-18-B-glycyrrhetic acid; 3-0-Acetyl-18-B-glycyrrhetic acid; Methyl 3-0-toxylglycyrrhetate; Biogastrone; Glycyrrhetinic acid phthalate; Lauroyl glycyrrhetinate; Methyl 3-oxoglycyrrhetate; Methyl-B-glycyrrhetinate; Sodium glycyrrhetinate; Methyl glycyrrhetate; 18-a-Glycyrrhetic acid; Glycyrrhizin; 11-Deoxo-18-B-glycyrrhetic acid; Glycyrrhetic acid; and Carbenoxolone sodium.

Glycyrrhizin and the virucidal analogues and derivatives thereof are referred to for convenience herein as glycyrrhizic triterpenoids abbreviated GTPD.

In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. R., *Can. Pharm. J.*, V118, No.9, 1985), and oral administration of glycyrrhizin contemporaneously with saponin antiinflamatory agents has been reported to inhibit saponin and saponigen hemolysis (Segal, R. et al., *Biochem. Pharmacol.* 26, 7 1977).

Inactivation of viruses, in vitro, under certain conditions, has been reported (see, e.g., Pompei, R., Exprientia (Switzerland) 36/3 1980). Such anti-viral activity as GTPD compounds sometimes exhibit has been attributed to reverse transcriptase-inhibitory activity (Nakashima, H. et al., *Jpn. J. Cancer. Res.* 78,8 1987) and to enhancement of interferon-gamma production (Shinada, M. et al., *Proc. Soc. Exp. Biol.* 181,2 1986), but the exact mechanism of the anti-viral function has not been confirmed.

Dargan, D. J., and Subak-Sharpe, J. H., (J. Gen. Virol., 1985-1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cocloxolone being the more potent anti-herpes agent, but no consistent effect on HSV DNA synthesis was identified. Some inhibiton of cellular DNA synthesis was observed, but this was relatively slight.

Csonka, G. W., and Tyrrell, D. A., (*Br. J. Vener. Dis.* 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188,2 1988), treatment of Epstein-Barr virus (EBV) infections (Van Benschoten M. M., *Am. J. Acupunct,* 16,1 1988), and in the treatment of chronic hepatitis (Fujisawa, K. et al., *Asian Med. J.* (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus. While GTPD drugs do, in some environments and under some conditions, exhibit some activity against some viruses, no anti-viral therapy based on GTPDs or in vitro anti-viral application of GTPDs has been generally accepted. It has been clearly demonstrated that vesicular stomatitis virus, one of the rhabdoviruses which has an envelope of glycoprotein, matrix protein and lipid, is inactivated. There is reason to believe that the GTPD compounds attack the lipid component of the virus envelope, but the nature of the attack on viruses has not been defined sufficiently to permit an accurate and specific categorization of the types and classes of viruses against which the GTPD compounds are effective. While it is believed that the GTPD compounds have some reactivity with and/or solubility in lipids and/or lipoproteins, and appear to attach to envelopes which contain lipids, these compounds are not properly considered as surfactants or detergents because red blood cells are not only not lysed, in low concentrations of GTPD compounds, but appear to be stabilized, and lipids are not dissolved.

It has been established that an exemplary triterpenoid compound, carbenoxolone and cicloxolone, as well as glycyrrhizic acid and derivatives thereof, typically in the form of salts, in a concentration range of from about 0.005 to 10 wt/%, effectively inactivates CMV by at least one log (one logarithmic factor). Solutions of glycyrrhizic compounds in the range of from about 0.5 to about 2 or 3 percent are presently considered optimal as to concentration.

The efficacy of the present methods are illustrated in the following example. 1-MRC-5 cells (Bartels) were grown in FCS and Eagle's minimal essential medium with 50 ug/ml of gentamicin, as the starting cell medium. 2-Cytomegalovirus (ATCC;$10^7$ tissue culture infectious dose (50) was added to three samples each of (a) the media, (b) whole blood A and (c) whole blood B. Glycyrrhizin in DMSO was added to one of the (a), (b) and (c) samples to a final concentration of 2 wt/%. Controls containing only media added to the same volume and DMSO in media were prepared. Six-hundred fold dilutions were used to infect MRC-% monolayers grown in glass coverslips inside glass vials. The inoculum was centrifuged at 1.000Xg for 1 hr. at room temperature, and 1 ml of fresh media was added to each vial. The cultures were incubated at 37° C. and observed daily for cytopathic effect. Seven-days post-infection the monolayers were fixed with methanol and stained by indirect fluorescent method using a CMV monoclonal antibody (Syva). No cytopathic effect was observed in the samples in which glycyrrhizin was present, while 34+cytopathic effect was observed in the other samples. Blood mixed with DMSO, and blood in media, tended to clot. Blood mixed with the glycyrrhizic compound did not clot, but slight hemolysis may have occurred. pH adjustments using KOH or NaOH, etc., may be required.

Of the readily available GTPD compounds, carbenoxolone is preferred for its anti-viral effectiveness. The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

It has been established that the exemplary GTPD compounds glycyrrhizin, carbenoxolone and cicloxolone added to a concentration of 1 W/% effectively reduces the CMV content by at least one log, carbenoxolone being about 100 times as effective at the 1 w/% concentration as the other exemplary GTPD compounds. In a comparable evaluation, a >3 log kill of HIV was achieved using a 1 w/% carbenoxolone treatment.

GTPD compounds, exemplary of which are carbenoxolone, glycyrrhizin and cicloxolone, are, according to this invention, used as antiviral or viral inhibitors by administration to the subject, the human patient or veterinary animal, as an aerosol for preventing and/or treating diseases resulting from infection by lipid-envelope containing viruses, chlamydiae and mycoplasma, including, most particularly such infectious diseases of the pulmonary system, and also including certain systemic diseases.

The GTPD compounds are dissolved in concentrations, typically of about 2 (+or−1.5) weight percent GTPD compound in a physiologically compatible carrier solvent. Such carriers may be of any composition which is physiologically compatible, which will dissolve and hold in solution a physiologically active concentration of GTPD, and which does not inactivate GTPD or interfere with the physiological efficacy of GTPD. Aqueous solutions, e.g. buffers, isotonic salt solutions, etc. may be used for some of the GTPD compounds; however, some of the GTPD compounds are not stable for long periods of time in aqueous solutions. Accordingly, non-aqueous solutions are preferred. Dimethyl sulfoxide (DMSO) is a widely used solvent and carrier for pharmaceutical reagents and is known to have some physiological effect; however, such physiological effect as DMSO does have does not interfere with the effectiveness of GTPD. DMSO solutions of one or more GTPD compounds, comprising from .005 to 10 weight percent, preferably from 0.5 to 3.5 weight percent total GTPD content, constitute a preferred class of compositions suitable for use in the methods of this invention. Other reagents which do not interfere with the absorption or efficacy of the GTPD compounds may be included in the solution. Antihistamines, analgesics, specific anti-microbials, etc., may, for example, be included in the aerosol. The following are examples of formulations in accordance with this invention:

Formula I

Carbenoxolone: 0.001 to 5 Wt/%
DMSO: 95 to 99.99 Wt/%

Formula II

Glycyrrhizin: 0.5 to 5 Wt/%
Isotonic saline: 95 to 99.5 Wt/%

Formula III

Cicloxolone: 0.5 to 5 Wt/%
Citrate buffer: 95 to 99.5 Wt/%

It is believed that there is a synergism between GTPD compounds and other antiviral agents which will result in a much greater than additive antiviral effect. Compositions such as the following are, accordingly, within the scope of this invention:

Formula IV

Carbenoxolone: 0.1 to 10 Wt/%
Ribavirin: 0.005 to 0.1 Wt/%
DMSO: 89.9 to 99.895 Wt/%

Formula V

Carbenoxolone: 0.1 to 10 Wt/%
Amantadine: 0.005 to 0.1 Wt/%
DMSO: 89.9 to 99.895 Wt/%

The formulations containing GTPD compounds is administered as an aerosol. The aerosol may be formed by releasing the compound, under pressure and mixed with a propellant such as propane, butane or one of the Freons, through a fine nozzle, by pumping the solution through a dispersing nozzle, etc., as is commonly done with inhalants. The particle size of the aerosol is not critical, but particles under about 3-5 microns in diameter are preferred for deep penetration into the pulmonary system. Continuous administation in a hospital environment or periodic administration, e.g. at 1 to 6 hour intervals, will allow the GTPD compounds to act effectively in the subject's pulmonary system.

In a variant but important form of inhalation therapy, GTPD compounds in the form of fine powder, alone or mixed with other powdered carriers, penetration anhancers or therapeutics which do not interfere substantially with the absorption and efficacy of GTPD compounds, i.e. powdered compositions consisting essentially of one of GTPD compounds, is insufflated into the bronchial and pulmonary cavities where it is absorbed directly through the tissues into the blood stream and where it may have local efficacy in the case of pulmonary diseases. One side advantage of this aspect of the invention is that GTPD compounds induce coughing which, in the case of particularly aged or infirm patients, may be of considerable therapeutic value in clearing the lungs of fluid, etc.

As a composition of matter, the invention may consist essentially of one or more glycyrrhizic triterpenoid compounds in intimate mixture with a solvent and/or a compound such as azone or the compounds disclosed by Rajadhyaksha, see e.g. U.S. Pat. Nos. 3,551,554; 3,989,816; 3,991,203; 4,122,170; 4,316,893; 4,415,563; 4,423,040; 4,424,210; 4,444,762 and 4,405,616, which enhances the penetration of said glycyrrhizic triterpenoid compounds through mammalian tissue and which may also include other non-interfering therapeutic compounds.

Precise formulations of the subject compositions and the use of such compositions, or the GTPD compounds alone or mixed together, in the treatment regimes will, of course, be determined based upon the particular disease for which prevention is sought or which is being treated, the weight of the subject, the efficacy of penetration enhancers, if used, and the criteria traditionally used in therapy.

Industrial Application

This invention is useful in clinical medicine and in veterinary medicine.

What is claimed:

1. A method for treating infectious diseases comprising introducing one or more glycyrrhizic triterpenoid compounds as an aerosol into the pulmonary system of the subject under treatment.

2. The method of claim 1 wherein the glycyrrhizic triterpenoid compounds are in the form of a fine powder and the introduction is accomplished by insufflation.

3. A method for treating infectious diseases comprising introducing carbenoxolone, glycyrrhizin or cicloxolones as an aerosol into the pulmonary system of the subject under treatment.

4. The method of claim 3 wherein said compounds are in the form of a fine powder and the introduction is accomplished by insufflation.

5. A method for treating or preventing infectious disease caused by a virus which comprises a lipid-containing envelope comprising introducing one or more glycyrrhizic triterpenoid compounds as a liquid aerosol or a fine powder into the pulmonary system of the subject under treatment.

6. The method of claim 5 wherein said compounds consist essentially of one or more of the compounds carbenoxolone, glycyrrhizin or cicloxolone.

* * * * *